United States Patent
Takada et al.

(10) Patent No.: US 10,269,536 B2
(45) Date of Patent: Apr. 23, 2019

(54) ELECTRON MICROSCOPE (71) Applicant: Hitachi High-Technologies Corporation, Minato-ku, Tokyo (JP)

(72) Inventors: Satoshi Takada, Tokyo (JP); Naomasa Suzuki, Tokyo (JP); Kazuo Aoki, Tokyo (JP); Takehiko Konno, Tokyo (JP); Takayuki Hoshino, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/554,812

(22) PCT Filed: Mar. 25, 2015

(86) PCT No.: PCT/JP2015/059019
§ 371 (c)(1),
(2) Date: Aug. 31, 2017

(87) PCT Pub. No.: WO2016/151786
PCT Pub. Date: Sep. 29, 2016

(65) Prior Publication Data
US 2018/0240643 A1  Aug. 23, 2018

(51) Int. Cl.
*H01J 37/244* (2006.01)
*H01J 37/14* (2006.01)
(Continued)

(52) U.S. Cl.
CPC ........ *H01J 37/244* (2013.01); *G01N 23/2252* (2013.01); *H01J 37/14* (2013.01);
(Continued)

(58) Field of Classification Search
CPC .......... H01J 37/244; H01J 37/28; H01J 37/20; H01J 37/26; H01J 37/08; H01J 37/12;
(Continued)

(56) References Cited

U.S. PATENT DOCUMENTS

| 7,105,816 B2 * | 9/2006 | Kamiya | H01J 37/244 |
| | | | 250/307 |
| 7,241,997 B2 * | 7/2007 | Odawara | G01T 1/1606 |
| | | | 250/336.2 |

(Continued)

FOREIGN PATENT DOCUMENTS

| JP | 57-73858 U | 5/1982 |
| JP | 8-83588 A | 3/1996 |

(Continued)

OTHER PUBLICATIONS

International Search Report (PCT/ISA/210) issued in PCT Application No. PCT/JP2015/059019 dated Jun. 16, 2015 with English translation (Four (4) pages).
Japanese-language Written Opinion (PCT/ISA/237) issued in PCT Application No. PCT/JP2015/059019 dated Jun. 16, 2015 (Five (5) pages).

*Primary Examiner* — David A Vanore
(74) *Attorney, Agent, or Firm* — Crowell & Moring LLP (57) ABSTRACT

The objective of the present invention is to simultaneously achieve image observations at a high resolution using an electron microscope, and X-ray analysis at a high energy-resolution using a microcalorimeter. An X-ray detector is disposed at a position where the intensity of the magnetic field from an objective lens is weaker than the critical magnetic field of a material used in a thermal insulation shield for a superconducting transition-edge sensor or a microcalorimeter. In addition, an optical system for transmitting X-rays to the detector is inserted between a sample and the detector. Alternatively, a magnetic field shield for shielding the X-ray detector is used.

14 Claims, 5 Drawing Sheets

(51) Int. Cl.
*H01J 37/28* (2006.01)
*G01N 23/2252* (2018.01)

(52) U.S. Cl.
CPC ........ *H01J 37/28* (2013.01); *G01N 2223/076* (2013.01); *G01N 2223/079* (2013.01); *H01J 2237/2445* (2013.01); *H01J 2237/24485* (2013.01)

(58) Field of Classification Search
CPC .......... H01J 37/06; H01J 37/09; H01J 37/141; H01J 37/1413; H01J 37/145; H01J 37/15; H01J 37/18; H01J 37/256; H01J 37/261; H01J 37/265; H01J 2237/24415; H01J 2237/2801; H01J 2237/032; H01J 2237/121; H01J 2237/2445; H01J 2237/0264; H01J 2237/028; H01J 2237/0475; H01J 2237/08; H01J 2237/0807; H01J 2237/103; H01J 2237/14; H01J 2237/1415; H01J 2237/1534; H01J 2237/188; H01J 2237/20; H01J 2237/201; H01J 2237/244; H01J 2237/24475; H01J 2237/2448; H01J 2237/2605; H01J 2237/28; H01J 2237/2802; H01J 2237/2807
USPC ...... 250/307, 311, 310, 336.2, 397, 396 ML, 250/306, 370.09, 396 R, 398, 423 F, 250/423 R, 492.21, 492.3, 493.1
See application file for complete search history.

(56) References Cited

U.S. PATENT DOCUMENTS

| | | | | |
|---|---|---|---|---|
| 7,910,888 B2* | 3/2011 | Tanaka | ................... | G01T 1/1606 250/336.2 |
| 7,939,801 B2* | 5/2011 | Kasai | .................... | H01J 37/141 250/307 |
| 8,049,182 B2* | 11/2011 | Bewick | ................... | H01J 37/09 250/396 ML |
| 8,334,511 B2* | 12/2012 | Schamber | ............. | H01J 37/244 250/306 |
| 8,563,944 B2* | 10/2013 | Shichi | ..................... | H01J 27/26 250/396 R |
| 9,536,703 B2* | 1/2017 | Agemura | .............. | H01J 37/244 |
| 10,014,151 B2* | 7/2018 | Imai | ....................... | H01J 37/12 |
| 2006/0104419 A1 | 5/2006 | Sasayama et al. | | |
| 2009/0184252 A1 | 7/2009 | Tanaka et al. | | |
| 2014/0175279 A1 | 6/2014 | Agemura | | |
| 2015/0255247 A1* | 9/2015 | Murakami | .............. | H01J 37/26 250/307 |
| 2018/0061613 A1* | 3/2018 | Sed'a | ..................... | H01J 37/20 |

FOREIGN PATENT DOCUMENTS

| | | |
|---|---|---|
| JP | 2005-257349 A | 9/2005 |
| JP | 2007-194292 A | 8/2007 |
| JP | 2008-39500 A | 2/2008 |
| JP | 2009-175117 A | 8/2009 |
| WO | WO 2013/018594 A1 | 2/2013 |

* cited by examiner

ELECTRON MICROSCOPE

TECHNICAL FIELD

The present invention relates to an electron microscope, by which a sample is irradiated with electron beams such that observation of the sample is performed, and an elemental analyzer using X-rays generated through irradiation with the electron beams.

BACKGROUND ART

There has been a technique in which characteristic X-rays generated when a sample is irradiated with electron beams by an electron microscope are detected, and thereby elemental analysis of the sample is performed. As an elemental analyzing technique, for example, energy dispersive X-ray spectrometry (EDS) has been widely known. In the EDS, a method of detecting X-rays by using a detection device made of semiconductor crystals such as silicon or germanium has been widely used.

In recent years, instead of a semiconductor detection device, a microcalorimeter (referred to as a TES type EDS) that has a higher energy-resolution than the semiconductor detection device and uses a transition edge sensor (TES) as the detection device has been used. In TES, a rapid change in resistance value occurs in proportion to incident energy generated when X-rays are incident, the change in resistance value is read as a current change of a circuit, and thereby the X-rays are detected. As a method of detecting the current change, there is known a method of using a superconducting quantum interference device (SQUID) installed in a cryogenic environment (for example, see PTL 1).

Also, in superconducting X-ray analyzer, in order to more efficiently detect X-rays without drawing out a cryogenic detector from a cooling machine main body, a technology of disposing an X-ray lens between a sample and a detection device is known (for example, see PTL 2).

CITATION LIST

Patent Literature

PTL 1: JP-A-2007-194292
PTL 2: JP-A-2005-257349 (Specification of US Patent Unexamined Application Publication No. 2006/0104419)

SUMMARY OF INVENTION

Technical Problem

In general, an electromagnetic lens is used as an objective lens in an electron microscope. In this case, an intense magnetic field permeates in the vicinity of the sample in order to focus electron beams on the sample. In a case of performing EDS in an electron microscope, it is desirable that, in terms of X-ray yields, a detection device is close to an electron-beam irradiating position. However, in a case of using a microcalorimeter using a SQUID type current detecting circuit in the EDS, the inventors found a problem in that a strong DC bias occurs due to an objective lens magnetic field and thus the current detecting circuit is saturated. The SQUID is a device suitable for detecting a minute magnetic field, and it is difficult to detect a minute change in resistance value of the microcalorimeter under a bias of intense magnetic field. In other words, since the SQUID type microcalorimeter is very vulnerable to an influence of a peripheral magnetic field, the SQUID type microcalorimeter is understood to be difficult to be applied as it is to the electron microscope that forms an intense magnetic field in the vicinity of the sample such that a sample is observed with a high resolution.

In order to avoid saturation of the current detecting circuit in the SQUID type microcalorimeter, a method of extending a distance between a sample and a detection device (SQUID) in order to avoid forming of an objective lens magnetic field is considered. However, in this case, X-ray yields are reduced, and thus the reduction in elemental analysis performance is unavoidable. PTL 2 discloses a technology in which the X-ray lens is disposed between the sample and the detection device in an electron microscope using the microcalorimeter; however, the device disclosed in PTL 2 is an X-ray analysis dedicated device and does not have a component such as an objective lens that forms an intense magnetic field in the vicinity of the sample, and thus it is needless to say that the detection device is not considered to be disposed so as not to be influenced from the magnetic field.

The objective of the present invention is to provide a technology for avoiding such an influence of a magnetic field from an objective lens and for using a microcalorimeter in an electron microscope. In other words, the objective of the present invention is to simultaneously achieve image observations at a high resolution using the electron microscope, and X-ray analysis at a high energy-resolution using a microcalorimeter.

Solution to Problem

In order to solve such the problem above, in the present invention, an X-ray detector is disposed in a space where the intensity of a magnetic field formed from an objective lens is weaker than a predetermined intensity of the magnetic field. More specifically, the X-ray detector is disposed at a position where the intensity of the magnetic field from the objective lens is weaker than the critical magnetic field of a material used in a thermal insulation shield for a superconducting transition-edge sensor or a microcalorimeter. In addition, an optical system for transmitting X-rays to the detector may be inserted between a sample and the detector. Alternatively, a magnetic field shield for shielding the X-ray detector may be used.

Advantageous Effects of Invention

According to the present invention, it is possible to avoid an influence of the magnetic field while avoiding a reduction in X-ray yields, and it is possible to perform elemental analysis using the microcalorimeter even in the electron microscope having the strong intensity of the magnetic field in the vicinity of the sample. In this manner, it is possible to simultaneously achieve image observations at a high resolution using the electron microscope, and X-ray analysis at a high energy-resolution using a microcalorimeter.

Problems, configurations, and effects other than the problems, configurations, and effects described above are clarified in the following description of embodiments.

DESCRIPTION OF EMBODIMENTS

Hereinafter, Examples of the present invention will be described in detail with reference to the figures.

Hereinafter, an example of using a scanning electron microscope as an example of an electron microscope will be described; however, the example is only an example of the present invention, and the present invention is not limited to an embodiment which will be described below. An example of the electron microscope in the present invention largely includes a device that captures an image of a sample using an electron beam. For example, the present invention is also applicable to a general-purpose scanning electron microscope, a sample processing device or a sample analyzer using the scanning electron microscope. Also, examples of an X-ray analyzing system using the electron microscope include an examination device, a review device, or a pattern measuring device using the scanning electron microscope. Hereinafter, the X-ray analyzing system using the electron microscope also includes a system in which the devices including the electron microscope are connected to one another via a network or an apparatus in which the devices are combined.

Hereinafter, in the specification, an example of the "sample" largely includes an object which is an observation and analysis target. For example, the example thereof also includes a semiconductor wafer formed of silicon or the like, a high-functional material of a lithium battery or the like, or a biological sample.

Example 1

Figure 1A:
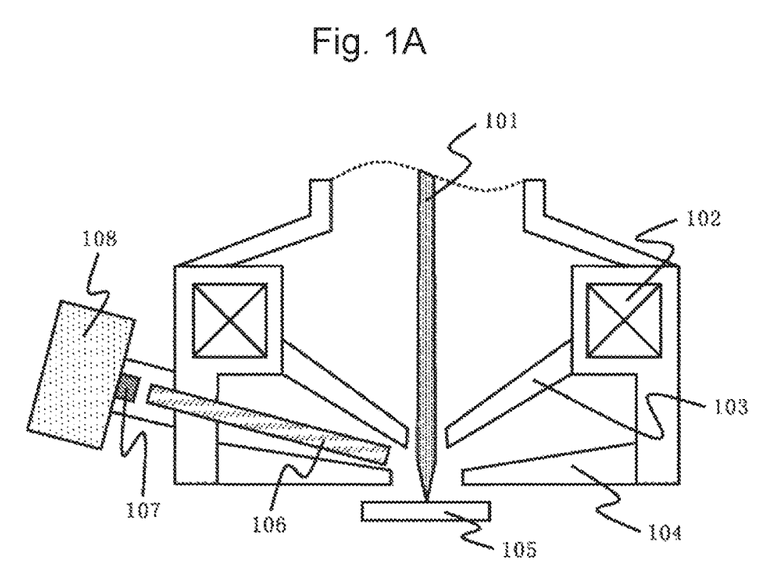
FIG. 1A is a view illustrating a configuration of an electron microscope and a microcalorimeter of Example 1.

Hereinafter, a first example will be described. FIG. 1A illustrates a configuration of an electron microscope and a microcalorimeter of the example. An electron beam 101 generated from an electron source (not illustrated) is deflected and focused by an electron optical system such that the sample is irradiated with the electron beam. More specifically, the electron beam is deflected by a scanning deflector (not illustrated) such that scanning on the sample is performed and is focused due to a magnetic field formed from an objective lens 102, and irradiation on a sample 105 is performed with the electron beam. The electron optical system includes the above-described scanning deflector, and the objective lens, and may also include another lens or an aligner, an electrode, or a detector, other than the deflector and the objective lens.

The electron microscope includes, in addition to the devices above, a control unit that controls operations of members and an image generating unit that generates an image based on a signal that is output from a detector (which are not illustrated). The control unit or the image generating unit may be configured as hardware by a dedicated circuit board, or may be configured as software that is executed by a computer connected to the electron microscope. In a case of a configuration as the hardware, the unit can be realized by integrating a plurality of computing elements that execute processes on a wiring board, or in a semiconductor chip or a package. In a case of a configuration as the software, the unit can be realized by mounting a high-speed general-purpose CPU in a computer and executing a program that executes desired arithmetic processing. An existing apparatus can be upgraded by a recording medium in which the program is recorded. Also, the apparatus, the circuit, and the computer are connected via a wired or wireless network and data is appropriately transmitted and received therebetween.

When the sample 105 is irradiated with the electron beam 101, secondary particles such as secondary electrons or reflected electrons are released from the sample. The secondary particles are detected by a secondary particle detector (not illustrated). An image processing unit configured of a computer or an image processing board associates a signal from the detector with an irradiation point on the sample with the electron beam, thereby forming an image of the sample. The image of the sample may be displayed on a display connected to the computer, or may be output as digital data to a storage device such as a hard disk or a memory.

Also, when the sample 105 is irradiated with the electron beam 101, a front surface of the sample 105 is excited, and characteristic X-rays that are specific for an excited element are generated. Irradiation with the characteristic X-rays is performed to a detector 107 of the microcalorimeter through an X-ray optical system 106. In other words, the X-ray optical system 106 transmits the X-rays generated from the sample to the detector 107 such that the X-rays are transmitted far away from a tip of a magnetic path of the objective lens 102. As will be described below, the detector 107 detects the X-rays generated from the sample and performs energy spectroscopy. In FIG. 1A and the following description, the detector is provided in a space between the X-ray optical system and the microcalorimeter; however, the detector may be in contact with and fixed to the X-ray optical system and the microcalorimeter. The X-ray optical system and the detector are physically fixed to each other, and thereby this is advantageous in that focus position alignment of the X-rays released from the X-ray optical system is unnecessary. Also, in FIG. 1A and the following description, an example in which the detector of the microcalorimeter is disposed outside the objective lens is described; however, as long as the detector is disposed at a position where the magnetic field is formed to be equal to or weaker than the critical magnetic field of a thermal insulation shield of the microcalorimeter, the detector may be disposed in the objective lens. In a case where the detector is installed at the position where the magnetic field is formed to be equal to or weaker than the critical magnetic field of the thermal insulation shield of the microcalorimeter, it is also possible to dispose the detector directly in the objective lens. On the other hand, also in a case where the detector is installed in a region in the objective lens where the magnetic field is formed not to be equal to or weaker than the critical magnetic field, it is also possible to control the intensity of the magnetic field on the periphery of the detector by providing a magnetic field shield, as in FIG. 3 which will be described below.

Figure 1B:
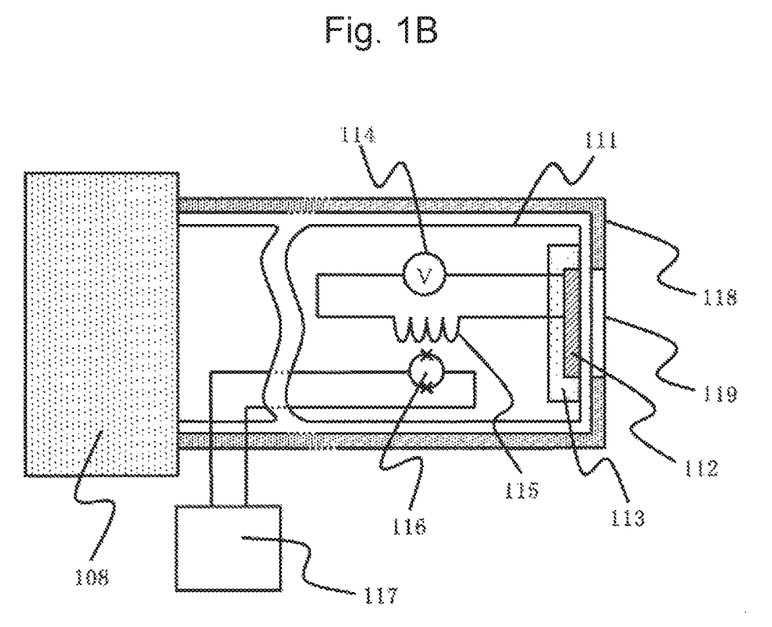
FIG. 1B is a view illustrating a configuration of a detector and a cooling machine of the microcalorimeter.

Next, with reference to FIG. 1B, a configuration of the detector 107 and a cooling machine 108 of the microcalorimeter will be described. A TES 112, a heatsink 113, a power supply 114, an inductor 115, a SQUID 116, and the like are provided in a housing 111 of the detector 107. The cooling machine 108 cools the TES 112 to a cryogenic temperature at which the TES enters a superconducting state. When the X-rays are incident on the TES 112, an amount of heat is generated depending on wavelengths of the X-rays and the TES 112 causes a rapid change in resistance value. The power supply 114 and the inductor 115 are connected to the TES 112, and a circuit is configured. When a resistance value of the TES 112 changes, a value of current flowing the circuit changes, and the change is detected by the SQUID 116 as a minute change in the magnetic field which occurs in the inductor 115. A SQUID circuit is connected to an analyzer 117. The analyzer 117 obtains a wavelength of the characteristic X-rays incident on the TES 112 by using the value of the current detected by the SQUID 116 and performs elemental identification of the sample. After the temperature of the TES 112 rises, the TES needs to be again cooled to the superconducting state in order to be able to perform the next measurement, and thus heat release is promoted to the heatsink 113 such that shortening of cooling time is achieved. Also, the housing 111 is made of metal such as copper having high heat conductivity, is connected to the cooling machine 108, and maintains the inside of the detector 107 (inside of the housing 111) in the superconducting state. A thermal insulation shield 118 is provided outside the housing 111 so as to cover the housing 111 and thermally blocks the inside of the detector from the outside thereof. The thermal insulation shield is provided with an opening on a front side such that the X-rays are incident on the TES 112 and a window 119 for maintaining a vacuum state therein is disposed.

In the example, the detector 107 is disposed at a position that is sufficiently separated from the magnetic field formed from the objective lens. The sufficiently separated position means a position at which the intensity of the magnetic field is weaker than a predetermined intensity of the magnetic field. More specifically, the position means a position at which the intensity of the magnetic field is weaker than the intensity of the critical magnetic field in which the superconducting state of the TES is destroyed. Also, in order to obtain the superconducting state suitable for using the TES, the microcalorimeter uses the thermal insulation shield and a superconductor (for example, niobium) is used as a shield material. In this case, the position may be a position at which the intensity of the magnetic field is weaker than the intensity of the critical magnetic field in which the superconducting state of the thermal insulation shield is destroyed. This is because the magnetic field does not permeate into the inside of the detector of the microcalorimeter when it is possible to maintain the intensity of the magnetic field weaker than the critical magnetic field in which the superconducting state of the thermal insulation shield is destroyed because of the expulsion of a magnetic field from the superconductor due to the Meissner effect. In the development of the electron microscope, calculation of the magnetic field profile is inevitable for the study on a shape of an electromagnetic lens, and it is possible to obtain a relationship between the disposition of the microcalorimeter and the intensity of the magnetic field applied to the TES by using results of the calculation.

A SQUID signal detected as the change in the amount of current by a circuit using the SQUID is transmitted to the analyzer (not illustrated), and energy of the characteristic X-rays is calculated based on the signal. Since the characteristic X-ray has an energy peak that is specific for an element, the characteristic X-rays are counted as spectra in which energy and the number of X-ray photons are plotted, and thereby it is possible to analyze which element exists at the irradiation position on the sample 105 with the electron beam 101. Elemental analysis results such as the spectra may be displayed on a display connected to the analyzer, or may be output as digital data to a storage device such as a hard disk or a memory. For example, the analyzer may be a hardware board, or may be realized by a program on a computer.

A line of magnetic force generated from the objective lens 102 is released in the vicinity of the sample 105 through an upper magnetic pole 103 and a lower magnetic pole 104 and an electromagnetic lens is formed. In the example, the X-ray optical system 106 is inserted through a space between the upper magnetic pole 103 and the lower magnetic pole 104. Although not illustrated, a tip of the X-ray optical system 106 on the sample side is provided with a light-receiving portion to which the X-rays are incident. The light-receiving portion may be a window or an opening. The X-ray optical system 106 may be components having the light-receiving portion to which the X-rays from the sample is incident and means that transmits the X-rays in the vicinity of the sample to the detector 107, or may be a combination of such components. For example, as the X-ray optical system 106, it is possible to use a poly-capillary lens as a bundle of glass capillaries having a very smooth inner wall. The X-rays incident on the poly-capillary lens are transmitted to the detector 107 of the microcalorimeter through the glass capillaries. Since the refractive index of the X-rays is an extent that is slightly smaller than 1, X-rays incident on the inner walls of the poly capillaries at a small angle can cause total reflection and can be transmitted without a loss of the intensity. The poly-capillary lens is preferable in that the critical angle, at which the total reflection is caused, depends on the energy of the X-ray; however, the critical angle is in a range of about several degrees to ten degrees and a wide range of energy bands can be converged by the same optical system. Also, an example in which the poly-capillary lens is used as the X-ray optical system is described; however, the X-ray optical system may be configured by combining a plurality of zone plates that have a quartz plate provided with concentric minute grooves and that cause the X-rays to converge thereon due to diffraction, or combining a plurality of total reflection mirrors.

Figure 2A:
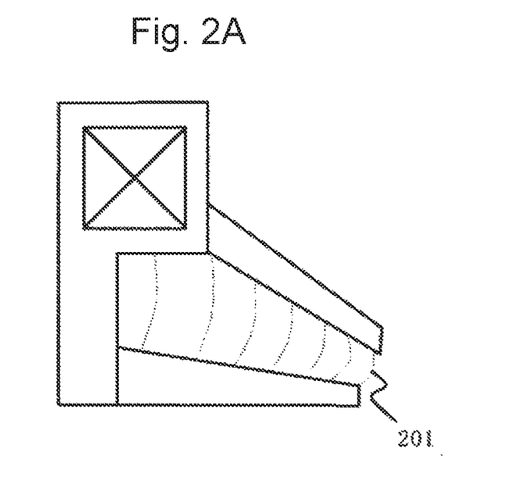
FIG. 2A is a schematic view illustrating distribution of a magnetic field formed on the periphery of the detector of the microcalorimeter which is formed from an objective lens of the electron microscope of Example 1.

Next, with reference to FIG. 2A, the magnetic field from the objective lens and an influence thereof on the microcalorimeter are described, and an advantage of disposing the X-ray optical system described above is clarified. FIG. 2A is a schematic view illustrating the distribution of the intensity of the magnetic field between the upper magnetic pole 103 and the lower magnetic pole 104. As described above, the line of magnetic force formed from the objective lens 102 is released in the vicinity of the sample 105 through the upper magnetic pole 103 and the lower magnetic pole 104. Hence, as a position is closer to the tips of the poles on the sample 105 between the upper magnetic pole 103 and the lower magnetic pole 104, the intensity of the magnetic field is stronger. In FIG. 2A, magnetic-field contour lines 201 are tied in a vertical direction of the paper surface along the upper magnetic pole 103 and the lower magnetic pole 104, and a state in which, as a position is recessed from the tips of the magnetic poles, the intensity of the magnetic field is weaker, is described.

Figure 2B:
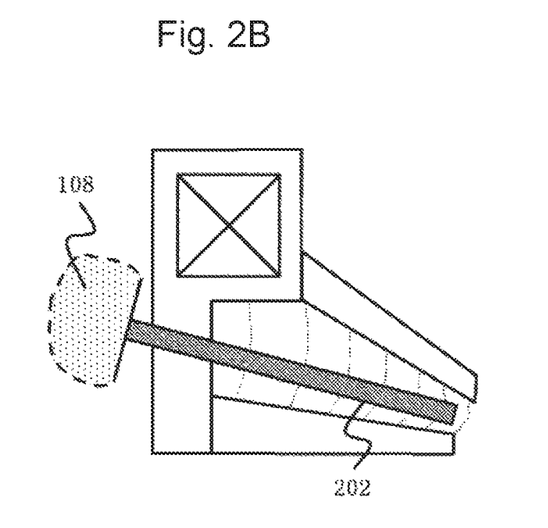
FIG. 2B is a view illustrating a relationship between the detector and the distribution of the magnetic field in a case where the detector of the microcalorimeter of Example 1 has a snout shape.

FIG. 2B, illustrates an example in which the detector 107 of the microcalorimeter has an elongated snout shape and the TES or the SQUID is disposed to be closer to the sample 105. FIG. 2B illustrates a comparative reference example of the example. Similar to the case in FIGS. 1A and 1B, a snout type detector 202 is cooled by the cooling machine 108. In a case where the X-ray optical system 106 is not used, the detector needs to be disposed as close to the sample 105 as possible in order to compensate X-ray yields; however, the detector is under the influence of the strong magnetic field of the objective lens 102 at the same time, a strong DC bias occurs to the SQUID, and thus it is difficult to detect a minute change in magnetic field due to the change in resistance value of the TES. As described in the example, the microcalorimeter is disposed to be sufficiently far from tip portions of the magnetic poles, and thereby there is an advantage of the present invention in that the influence of the magnetic field is avoided and it is possible to avoid the reduction in the X-ray yields due to the X-ray optical system 106.

In a case where the semiconductor wafer is the sample, a molecular structure of a material of a resist material for exposing a semiconductor circuit pattern is likely to change by damage due to the irradiation with the electron beams. On the other hand, the high resolution is achieved in the electron microscope due to the minuteness of the semiconductor pattern. In order to achieve the high resolution while the damage to the material is controlled, the irradiation energy of the electron beam is reduced and it is necessary to increase focus performance of the lens by extremely reducing a working distance of the objective lens. In such a case, the objective lens may have a shape described in the example. In other words, it is preferable that the lower magnetic pole 104 of the objective lens 102 is disposed to be parallel to the sample 105 and a distance between the lower magnetic pole 104 and the sample 105 is very small. In a case of employing the objective lens having such a configuration, it is physically difficult to provide, between the lower magnetic pole 104 and the sample 105, the X-ray optical system that transmits the X-rays to the detector 107 of the microcalorimeter. Hence, in such a case, it is desirable to employ a method of transmitting the X-rays from a position between the upper magnetic pole 103 and the lower magnetic pole 104 as described in the example or a method of transmitting the X-rays from a position above the upper magnetic pole 103 to be described in Example 3.

Example 2

Next, a second example will be described with reference to FIG. 3. The second example is an example in which the detector is shielded from the magnetic fields formed from the objective lens by using a magnetic field shield that covers the detector, and the detector is directly inserted between the upper magnetic pole and the lower magnetic pole of the objective lens. Hereinafter, the description of the same portions as those in Example 1 is omitted.

Figure 3:
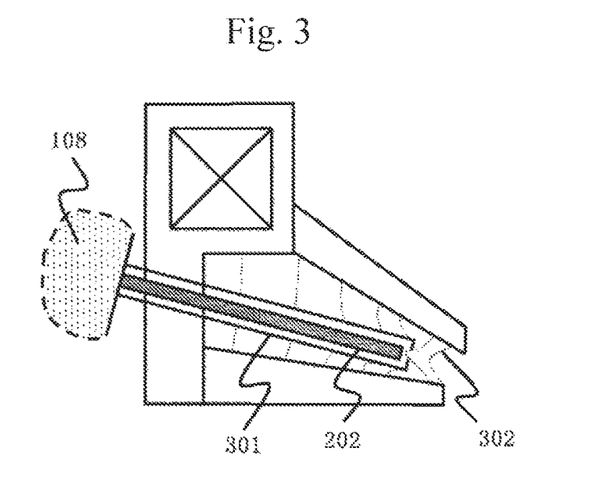
FIG. 3 is a view illustrating a relationship between a detector and distribution of a magnetic field of Example 2.

FIG. 3 illustrates an example in which a magnetic field shield 301 is disposed to cover the snout type detector 202 in FIG. 2B. At least a part of the snout type detector 202 (that is, a portion having a snout shape) is disposed between the upper magnetic pole and the lower magnetic pole of the objective lens. Even when the detector has a snout shape, the shapes and disposition of configurational elements such as the TES or the SQUID included inside the detector are as illustrated in FIG. 1B without any substantial change. The magnetic field shield 301 in FIG. 3 covers at least the entire region disposed between the magnetic poles of the objective lens of the snout type detector 202, and has a shape in which only the tip portion of the snout type detector 202 in the vicinity of the sample is provided with an opened window such that the X-rays are incident. However, the shape of the magnetic field shield is not limited to the shape in the figure, but the magnetic field shield may have a shape such that a magnetic field that has the intensity to influence the TES in the magnetic field shield 301 does not enter the magnetic field shield. Specifically, the distribution of the intensity of the magnetic field like a contour line 302 is obtained by using a magnetic field simulator, and thereby the shape may be calculated.

As described in Example 1, the detector 107 of the microcalorimeter extends to have the snout shape, and thereby the TES or the SQUID can be close to the sample 105. Thus, it is possible to expect improvement of the X-ray yields. However, in practice, since the strong magnetic field is applied to the tip of the objective lens, a problem exists in that it is difficult to use the microcalorimeter. In the example, a metal such as permalloy having high magnetic permeability is used in the magnetic field shield 301 and the entire snout type detector 202 is covered. In this manner, the magnetic field is obstructed by the magnetic field shield 301 as represented by the magnetic-field contour line 302 in FIG. 3, and it is possible to reduce the intensity of the magnetic field that is applied to the snout type detector 202. In this manner, an installation range, in which the microcalorimeter can operate, can be close to the sample, and thus it is possible to expect the improvement of the X-ray yields. As described in Example 1, the installation range, in which the microcalorimeter can operate, can be close to the sample is a range in which the intensity of the magnetic field is the critical magnetic field in which the superconducting state of the TES is destroyed or is weaker than the critical magnetic field of the thermal insulation shield in the superconducting state. Specifically, the distribution of the intensity of the magnetic field like the contour line 302 is obtained by using the magnetic field simulator, and thereby the shape of the magnetic field shield 301 and a range in which it is possible to install the tip of the snout type detector 202 may be calculated.

The X-ray optical system as described in Example 1 is further added to the example, and thereby it is possible to expect the further improvement of yields.

According to the example, since it is possible to dispose the detector of the microcalorimeter in the strong magnetic field, it is possible to perform the elemental analysis with high X-ray yields even without using the X-ray optical system.

Example 3

Next, a third example will be described with reference to FIGS. 4A and 4B. The third example is an example in which the X-ray optical system is disposed on an upper side (electron source side) of an upper magnetic path of the objective lens. Hereinafter, the description of the same portions as those in Examples 1 or 2 is omitted.

Figure 4A:
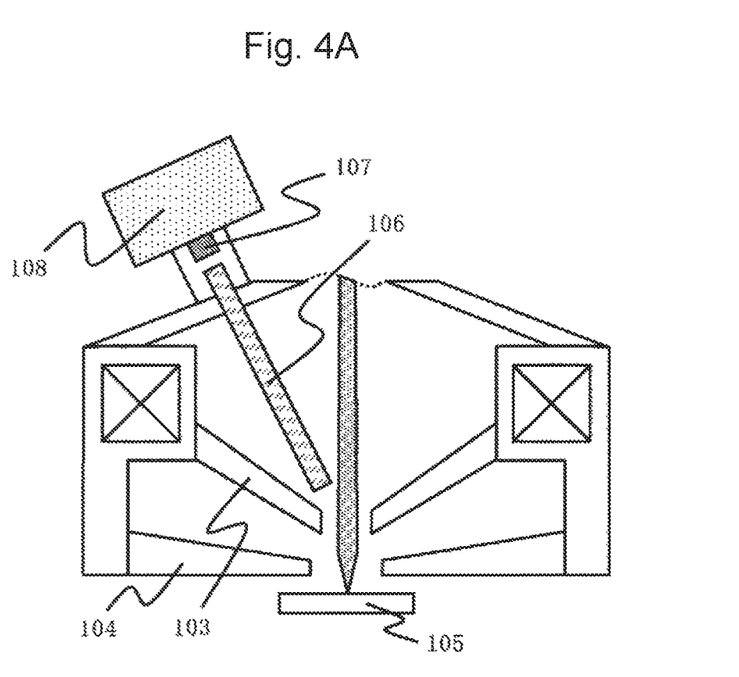
FIG. 4A is a view illustrating a configuration of an electron microscope and a microcalorimeter of Example 3.

FIG. 4A illustrates an example in which the detector of the microcalorimeter is disposed to transmit the X-rays from above the upper magnetic pole 103. The X-ray optical system 106 is disposed on the electron source side from the objective lens (more specifically, on the electron source side from the upper magnetic pole of the objective lens). Also, as illustrated in FIG. 4B, the X-ray optical system 106 is disposed in the magnetic field formed from the upper magnetic pole 103. FIG. 4A illustrates an example in which the X-ray optical system 106 is disposed immediately above the upper magnetic pole 103 of the objective lens in a direction parallel to the upper magnetic pole 103; however, the disposition of the X-ray optical system 106 is not limited thereto. For example, another component may be present between the X-ray optical system 106 and the upper magnetic pole 103, or the X-ray optical system 106 may not have a straight line shape. Similar to the case of Example 1, in order to avoid the influence of the magnetic field from the objective lens, the microcalorimeter is disposed at a position (position at which the intensity of the magnetic field is weaker than the predetermined intensity of the magnetic field) that is sufficiently separated from the tip portions of the magnetic poles. Thus, as in the example, the X-ray optical system 106 is inserted between the sample 105 and the detector 107, and thereby it is possible to avoid the reduction of the X-ray yields.

Figure 4B:
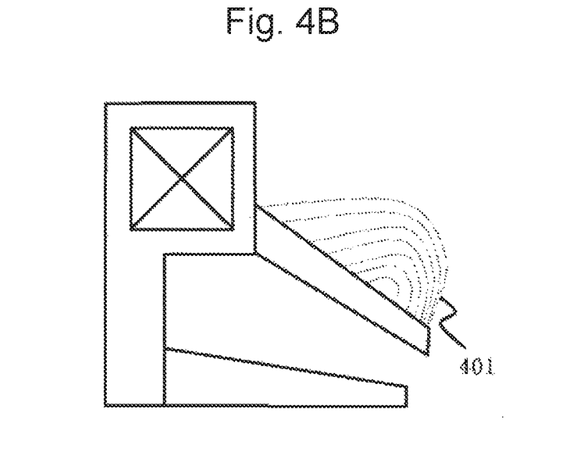
FIG. 4B is a view illustrating distribution of a magnetic field formed on the periphery of a detector of the microcalorimeter which is formed from an objective lens of the electron microscope of Example 3.

FIG. 4B is a schematic view illustrating the distribution of the intensity of the magnetic field from the objective lens in which the magnetic field leaks upward from the upper magnetic pole 103. Similar to the case in Example 1, the distribution in which the intensity of the magnetic field is stronger as the position is closer to the tip of the pole is represented by a contour line 401. Hence, when the detector 107 has the snout shape and is close to the sample 105, similar to FIG. 2B even when the detector is disposed from the upper side of the upper magnetic pole of the objective lens, the microcalorimeter is difficult to operate due to the influence of the magnetic field formed from the objective lens.

Compared to the case in Example 1, the example is disadvantageous in terms of the X-ray yields, because the disposition of the X-ray optical system 106 is restricted by the physical dimension of the objective lens and a distance between the X-ray optical system 106 and the sample 105 extends. However, the X-rays are taken at a high angle, and thereby it is advantageous in that it is possible to detect the X-rays, a small amount of which is absorbed in the sample.

Example 4

Next, a fourth example will be described with reference to FIGS. 5A and 5B. Unlike Examples 1 to 3, the fourth example is an example of an electron microscope including an out-lens type objective lens having an objective lens shape. Hereinafter, the description of the same portions as those in Examples 1 to 3 is omitted.

Figure 5A:
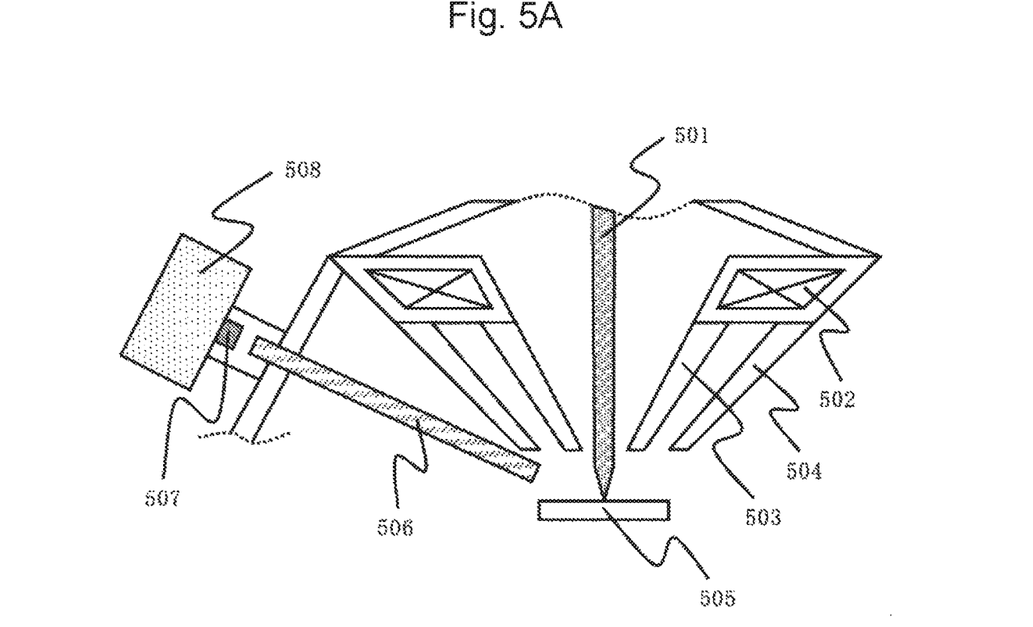
FIG. 5A is a view illustrating a configuration of an electron microscope and a microcalorimeter of Example 4.

FIG. 5A illustrates a configuration of an electron microscope and a microcalorimeter of the example. Similar to the case in Example 1, electron beams 501 released from the electron source (not illustrated) are focused due to the magnetic field formed from an objective lens 502, and a sample 505 is irradiated with the electron beams. The characteristic X-rays generated from the sample 505 are transmitted by an X-ray optical system 506 and are incident on a detector 507 of the microcalorimeter. In FIG. 5A, the X-ray optical system 506 is disposed on the sample side from the objective lens (more specifically, on the sample side from a lower magnetic pole 504 of the objective lens). Also, as illustrated in FIG. 5B, the X-ray optical system 506 is disposed in the magnetic field formed from the lower magnetic pole 504 between the sample 505 and the lower magnetic pole 504. The detector 507 is cooled by a cooling machine 508.

In the example, the magnetic poles of the objective lens 502 are disposed downward, and have an out-lens type lens shape in which a focus effect is applied to the electron beam 501 below the tips of the magnetic poles. In a case where a sample stage (not illustrated), on which the sample is mounted, includes a tilt mechanism, the upper magnetic pole 503 and the lower magnetic pole 504 are disposed at an angle with respect to the sample 505, and thereby the example is characterized in that it is possible to tilt the sample 505 by the sample stage and to observe the sample. On the other hand, it is necessary to reduce the lens for performing the tilt observation, and thus the microcalorimeter is disposed so as to transmit the X-rays from the lower side (sample side) of the lower magnetic pole 504. Similar to the cases of Examples 1 and 3, in order to avoid the influence of the magnetic field from the objective lens, the microcalorimeter is disposed at a position (position at which the intensity of the magnetic field is weaker than the predetermined intensity of the magnetic field) that is sufficiently separated from the tip portions of the magnetic poles. Thus, as in the example, the X-ray optical system 506 is inserted between the sample 505 and the detector 507, and thereby it is possible to avoid the reduction of the X-ray yields.

Figure 5B:
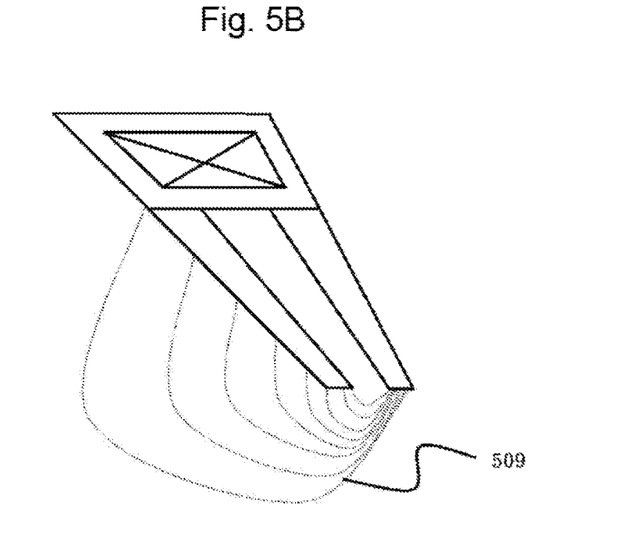
FIG. 5B is a view illustrating distribution of a magnetic field formed on the periphery of the detector of the microcalorimeter which is formed from an objective lens of the electron microscope of Example 4.

FIG. 5B is a schematic view illustrating the distribution of the intensity of the magnetic field from the objective lens in the example. Similar to the case in Examples 1 and 3, the distribution in which the intensity of the magnetic field is stronger as the position is closer to the tip of the pole is represented by a contour line 509. Hence, when the detector 507 has the snout shape and is close to the sample 505, similar to FIG. 2B even when the detector is disposed from the lower side of the lower magnetic pole of the objective lens, the microcalorimeter is difficult to operate due to the influence of the magnetic field formed from the objective lens.

In the example, the objective lens 502 has the out-lens shape, and thereby the operation distance of the objective lens extends, in which, in terms of focus performance of lens, that is, a resolution of the electron microscope, it is possible to be more disadvantageous than the cases of Examples 1 to 3. On the other hand, compared to the cases of Examples 1 and 2, there is a distance between the sample 505 and the tips of the magnetic poles, and thus it is possible to broaden the light receiving portion of the X-ray optical system 506 of the microcalorimeter, the sample 505 is tilted, and thereby apparent permeation lengths of the electron beams 501 are short. Thus, the example is advantageous in that it is possible to increase an amount of the characteristic X-rays generated from the front surface of the sample 505.

The present invention is not limited to the examples described above, and includes various modification examples. For example, the examples are described in detail for an easy understanding of the present invention, and the present invention is not necessarily limited to inclusion of the entire configurations described above. Also, it is possible to replace a part of a configuration of an example with a configuration of another example, and it is possible to add a configuration of an example to a configuration of another example. Also, it is possible to add another configuration to, to remove, or to replace, with another configuration, a part of each of the configurations of the examples.

For example, in FIGS. 1A, 1B, 4A, 4B, 5A, and 5B, an example in which the detector of the microcalorimeter is disposed outside the objective lens is described; however, as long as the detector is disposed at a position where the magnetic field is formed to be equal to or weaker than the critical magnetic field of the superconducting shield of the microcalorimeter, the detector may be disposed in the objective lens. At this time, the magnetic field shield as in FIG. 3 is provided, and thereby it is possible to control the intensity of the magnetic field on the periphery of the detector. However, in a case where the magnetic field shield can be disposed at a position where the magnetic field is equal to or lower than the critical magnetic field of the superconducting shield of the microcalorimeter, the magnetic field shield may not be provided.

REFERENCE SIGNS LIST

101: electron beam
102: objective lens
103: upper magnetic pole
104: lower magnetic pole
105: sample
106: X-ray optical system
107: detector
108: cooling machine
111: housing
112: TES
113: heatsink
114: power supply
115: inductor
116: SQUID
117: analyzer
118: thermal insulation shield
119: window
201: magnetic-field contour line
202: snout type detector
301: magnetic field shield
302: magnetic-field contour line
401: magnetic-field contour line
501: electron beam
502: objective lens
503: upper magnetic pole
504: lower magnetic pole
505: sample
506: X-ray optical system
507: detector
508: cooling machine
509: magnetic-field contour line

The invention claimed is:

1. An electron microscope comprising:
an electron source that generates an electron beam;
an objective lens that focuses the electron beam on a sample;
an X-ray detector that detects X-rays generated from the sample and performs energy spectroscopy; and
an X-ray optical system that transmits X-rays generated from the sample to the X-ray detector such that the X-rays are transmitted far away from a tip of a magnetic path of the objective lens,
wherein the X-ray detector is disposed in a space where the intensity of a magnetic field formed from the objective lens is weaker than a predetermined intensity of the magnetic field.

2. The electron microscope according to claim 1,
wherein the x-ray detector includes a superconducting transition-edge sensor.

3. The electron microscope according to claim 2,
wherein the predetermined intensity of the magnetic field is the intensity of the critical magnetic field in which a superconducting state of the superconducting transition-edge sensor is destroyed.

4. The electron microscope according to claim 2,
wherein the X-ray detector has a thermal insulation shield made of a superconducting material, and
wherein the predetermined intensity of the magnetic field is the intensity of the critical magnetic field in which a superconducting state of the thermal insulation shield is destroyed.

5. The electron microscope according to claim 1,
wherein the X-ray detector is a microcalorimeter.

6. The electron microscope according to claim 1,
wherein the X-ray optical system is a poly-capillary lens.

7. The electron microscope according to claim 1,
wherein the X-ray optical system is disposed between an upper magnetic path and a lower magnetic path of the objective lens.

8. The electron microscope according to claim 1,
wherein the X-ray optical system is disposed on the electron source side from the upper magnetic path of the objective lens in a magnetic field formed by the upper magnetic path.

9. The electron microscope according to claim 1,
wherein the X-ray optical system is disposed on the sample side from the lower magnetic path of the objective lens in a magnetic field formed by the lower magnetic path.

10. The electron microscope according to claim 1,
wherein a lower magnetic path of the objective lens is disposed to be parallel to the sample.

11. An electron microscope comprising:
an electron source that generates an electron beam;
an objective lens that focuses the electron beam on a sample;
an X-ray detector that detects X-rays generated from the sample and performs energy spectroscopy; and
a magnetic field shield that shields the X-ray detector from a magnetic field formed from the objective lens,
wherein the X-ray detector is disposed in a space where the intensity of a magnetic field formed from the objective lens due to the magnetic field shield is weaker than a predetermined intensity of the magnetic field; and
wherein at least a part of the X-ray detector is disposed between an upper magnetic path and a lower magnetic path of the objective lens.

12. The electron microscope according to claim 11,
wherein the x-ray detector includes a superconducting transition-edge sensor.

13. The electron microscope according to claim 12,
wherein the predetermined intensity of the magnetic field is the intensity of the critical magnetic field in which a superconducting state of the superconducting transition-edge sensor is destroyed.

14. An electron microscope comprising:
an electron source that generates an electron beam;
an objective lens that focuses the electron beam on a sample;
an X-ray detector that detects X-rays generated from the sample and performs energy spectroscopy; and
a magnetic field shield that shields the X-ray detector from a magnetic field formed from the objective lens,
wherein the X-ray detector is disposed in a space where the intensity of a magnetic field formed from the objective lens due to the magnetic field shield is weaker than a predetermined intensity of the magnetic field;

wherein the x-ray detector includes a superconducting transition-edge sensor; and wherein the X-ray detector has a thermal insulation shield made of a superconducting material, and wherein the predetermined intensity of the magnetic field is the intensity of the critical magnetic field in which a superconducting state of the thermal insulation shield is destroyed.

* * * * *